United States Patent
Beach et al.

(10) Patent No.: US 11,760,905 B2
(45) Date of Patent: Sep. 19, 2023

(54) METHOD AND APPARATUS TO SCREEN FOR AND MONITOR CEREBROVASCULAR STENOSIS AND FOR NONINVASIVE INTRACRANIAL PRESSURE MEASUREMENT

(71) Applicant: NIHON KOHDEN CORPORATION, Tokyo (JP)

(72) Inventors: Kirk Watson Beach, Seattle, WA (US); Mitsuhiro Oura, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1117 days.

(21) Appl. No.: 16/345,115

(22) PCT Filed: Nov. 1, 2017

(86) PCT No.: PCT/US2017/059583
§ 371 (c)(1),
(2) Date: Apr. 25, 2019

(87) PCT Pub. No.: WO2018/085439
PCT Pub. Date: May 11, 2018

(65) Prior Publication Data
US 2019/0282108 A1    Sep. 19, 2019

Related U.S. Application Data

(60) Provisional application No. 62/415,539, filed on Nov. 1, 2016.

(51) Int. Cl.
*C09J 7/20* (2018.01)
*A61B 5/257* (2021.01)
(Continued)

(52) U.S. Cl.
CPC ............... *C09J 7/20* (2018.01); *A61B 5/257* (2021.01); *A61B 8/4236* (2013.01);
(Continued)

(58) Field of Classification Search
None
See application file for complete search history.

(56) References Cited

U.S. PATENT DOCUMENTS

| 5,951,476 A | 9/1999 | Beach |
| 2002/0049384 A1 | 4/2002 | Davidson et al. |

(Continued)

FOREIGN PATENT DOCUMENTS

| EP | 1 958 569 A1 | 8/2008 |
| EP | 3 496 620 A1 | 6/2019 |

(Continued)

OTHER PUBLICATIONS

International Search Report and Written Opinion of the International Search Report for PCT/US2017/059583 dated Feb. 16, 2018.
(Continued)

*Primary Examiner* — Frank D Ducheneaux
(74) *Attorney, Agent, or Firm* — KENEALY VAIDYA LLP

(57) ABSTRACT

Brain motion monitoring systems and methods are disclosed that can detect interpret and/or display normal and abnormal brain motions. The devices and methods can detect Cerebrovascular Stenosis and provide for Noninvasive Intracranial Pressure Measurement.

7 Claims, 15 Drawing Sheets

(51) Int. Cl.
*A61B 8/00* (2006.01)
*B32B 43/00* (2006.01)
*B32B 38/00* (2006.01)

(52) U.S. Cl.
CPC .......... *A61B 8/4281* (2013.01); *B32B 43/006* (2013.01); *B32B 2038/0088* (2013.01); *C09J 2301/124* (2020.08); *C09J 2301/308* (2020.08); *Y10T 428/28* (2015.01)

(56) References Cited

U.S. PATENT DOCUMENTS

| | | |
|---|---|---|
| 2002/0062078 A1 | 5/2002 | Crutchfield et al. |
| 2002/0077549 A1 | 6/2002 | Davidson et al. |
| 2002/0091320 A1 | 7/2002 | Crutchfield et al. |
| 2002/0099291 A1 | 7/2002 | Davidson et al. |
| 2004/0002654 A1 | 1/2004 | Davidson et al. |
| 2004/0006488 A1 | 1/2004 | Fitall et al. |
| 2004/0049105 A1 | 3/2004 | Crutchfield et al. |
| 2004/0152984 A1 | 8/2004 | Crutchfield et al. |
| 2005/0020945 A1 | 1/2005 | Tosaya et al. |
| 2005/0038342 A1 | 2/2005 | Mozayeni et al. |
| 2006/0106311 A1 | 5/2006 | Lo et al. |
| 2007/0016046 A1 | 1/2007 | Mozayeni et al. |
| 2010/0234733 A1 | 9/2010 | Wahlheim |
| 2013/0245483 A1 | 9/2013 | Eichler |
| 2013/0338544 A1 | 12/2013 | Newell |
| 2014/0180046 A1 | 6/2014 | Campbell et al. |
| 2015/0359448 A1 | 12/2015 | Beach |
| 2018/0154187 A1 | 6/2018 | Newell |
| 2019/0175141 A1 | 6/2019 | Rosengart |

FOREIGN PATENT DOCUMENTS

| | | |
|---|---|---|
| JP | 2002-010986 A | 1/2002 |
| JP | 2006-000161 A | 1/2006 |
| JP | 2008-534071 T | 8/2008 |
| JP | 2015-519970 T | 7/2015 |
| WO | 2015/191902 A1 | 12/2015 |
| WO | 2016/092414 A1 | 6/2016 |
| WO | 2018/031477 A1 | 2/2018 |
| WO | 2018/085439 A1 | 5/2018 |

OTHER PUBLICATIONS

The Partial Supplementary European Search Report for the related European Patent Application No. 17866733.3 dated May 8, 2020.
The extended European Search Report for the related European Patent Application No. 17866733.3 dated Jun. 9, 2020.
Venkatakrishna Rajajee et al: "OpticNerve Ultrasound for the Detection of Raised Intracranial Pressure", Neurocritical Care, Humana Press Inc, NewYork vol. 15, No. 3, Jul. 19, 2011 (Jul. 19, 2011), pp. 506-515.
Xiaobin Xie et al: "Noninvasive intracranial pressure estimation by orbital subarachnoid space measurement: the Beijing Intracranial and Intraocular Pressure (iCOP) study", Critical Care, Biomed Central Ltd., London, GB, vol. 17, No. 4, Jul. 24, 2013 p. R162.
Japanese Office Action (Decision to Refusal) for the related Japanese Patent Application No. 2019-522645 dated May 11, 2021.

METHOD AND APPARATUS TO SCREEN FOR AND MONITOR CEREBROVASCULAR STENOSIS AND FOR NONINVASIVE INTRACRANIAL PRESSURE MEASUREMENT

CROSS-REFERENCE TO RELATED APPLICATIONS

This application is a U.S. National Stage Application under 35 U.S.C § 371 of International Patent Application No. PCT/US2017/059583 filed Nov. 1, 2017, which claims the benefit of priority to U.S. Provisional Application No. 62/415,539 filed Nov. 1, 2016, the disclosures of all of which are hereby incorporated by reference in their entireties.

BACKGROUND

In the US: 1,700,000 people have a head injury each year, 275,000 are hospitalized for head injury, 1,000,000 have hydrocephalus, 500,000 have brain tumor and nearly 1,000,000 have cerebral edema for other reasons. All of these patients could potentially benefit from the evaluation of intracranial pressure (ICP), but the standard invasive measurement method requires neurosurgical trepanation. Potential complications include infection (7.4%) and hemorrhage. Thus invasive ICP measurement is only performed in the most critical cases.

One of the great barriers to invasive ICP measurements is that these measurements are only performed at specialized neurosurgical centers. Many critical care facilities and emergency care facilities, far from neurosurgical centers are presented with cases that might benefit from evaluation for brain swelling or expanding mass within the skull resulting in elevated ICP. The noninvasive method of the presently disclosed subject matter can provide critical information for both urgent and chronic measurements to optimize patient triage and management.

In the US each year: 100,000 people have unexpected hemorrhagic stroke, an estimated 250,000 have unheralded primary atheroembolic stroke and an estimated 250,000 have unheralded primary thromboembolic stroke. The atheroembolic strokes can be prevented by identifying and treating the atheromas vulnerable to rupture which will cause these strokes. Severe flow reducing stenoses in the carotid arteries are likely benign because alternate collateral arterial pathways compensate for the arterial obstruction; the extreme hemodynamic forces are absent on such anatomic stenoses. In contrast, pressure reducing stenoses, in which no collateral alternatives are present to provide mandatory flow to the regions of the cerebral endorgan, do experience extreme forces likely to lead to catastrophic eruption and atheroembolic stroke.

Although most publications refer to atherosclerotic plaque, the term atheroma is used here because it invokes a more accurate understanding of the process. An atherosclerotic stenosis is caused by a monoclonal tumor in of the medial layer of the artery wall. The growth of these tumors is limited to a maximum thickness of 1.5 mm by diffusion: this is the generally accepted maximum thickness of the media (IMT, Intima-Media Thickness) based on epidemiological studies. To grow further, as in cancerous tumors, the atheroma must begin to secrete a hormonal angiogenic factor. The presence of this neovascular network, supplied by arterioles and drained by venules from the vasa vasorum coming from the arterial adventitial sheath provide the hydraulic mechanism for atheroma expansion and rupture.

A severe stenosis is often called "hemodynamically significant" if it causes a "reduction in pressure or flow". However a reduction in pressure is very different from a reduction in flow. A flow reduction is only possible if an alternate collateral pathway exists to supply the mandatory flow required by the endorgan. In that case, the flow through the stenosis is reduced to such an extent that the pressure from proximal to distal is not reduced severely. In contrast, a pressure reducing stenosis has no alternative collateral pathway to supply the endorgan; to sustain the required flow rate, the endorgan vasodilates to lower the resistance to flow, causing a pressure drop from proximal to distal across the stenosis. A "normal" systolic and diastolic blood pressure of 120/80 proximal to the stenosis might be reduced to 60/50 distal to the stenosis. The flow energy is dissipated by turbulence in the non-streamlined region distal to the stenosis. In addition, if the velocities in the stenosis exceed 3.5 m/s, Bernoulli and Coanda pressure depressions in the stenosis serve to draw blood into the neovascular core of the atheroma. This is sometimes called intraplaque hemorrhage and is considered to be an anatomic marker for "vulnerable plaque".

At present, carotid endarterectomy is recommended for all patients identified with severe carotid stenosis resulting in 140,000 carotid endarterectomy or stents per year. Only 1/17 of those patients would have a stroke if untreated; thus only an estimated 8,400 strokes are prevented in the US each year by this method. Currently, screening for arterial stenosis to prevent stroke is not recommended because neither screening studies nor practice differentiates those stenosis caused by vulnerable atheroma from those caused by benign atheroma. In addition, the only currently available screening method is ultrasonic carotid duplex Doppler examination, a method that is expensive. This invention is designed to identify only those patients with stenoses vulnerable to rupture causing atheroembolic stroke.

Among people over the age of 50, about 1/500 are at risk for atheroembolic stroke. For an economically viable screening program for such people, the cost of screening must be near the cost of measuring blood pressure or obtaining a diagnostic electrocardiograph waveform.

The ultimate goal is to prevent stroke. Prevention of primary (first unheralded) stroke is the most elusive goal. This requires screening of the population, potentially selecting those at greatest risk. According to both the US Preventative Services Task Force (USPSTF) and the UK National Institute for Clinical Excellence (NICE); at present, screening is not recommended for the prevention of thromboembolic stroke, atheroembolic stroke, or hemorrhagic stroke, but is recommended for prevention of Abdominal Aortic Aneurysm (AAA) rupture in people over the age of 50.

| Estimate of Screening Parameters | | |
|---|---|---|
| | AAA | Stroke |
| Incidence of Diagnosis | 5/100,000/yr | 140,000/yr, 41/100,000/yr |
| Incidence of Death | 15,000/year, 4.4/100,000/year | 150,000/year, 44/100,000/year |
| Incidence of Permanent Disability | 0 | 150,000/year, 44/100,000/year |
| Incidence of primary event | 15,000/year, 4.4/100,000/year | 600,000/year, 264/100,000/year |
| Test Sensitivity & Specificity | 100% & 100% | ~50%, ~6% |
| Treatment Efficacy | ~100% | ~50% for atheroembolic stroke |

Although the problem of stroke is much larger than AAA in all respects, at present, there is no low cost effective screening test.

Screening for risk of stroke is not currently recommended. There are 5 screening methods in current use that were considered when formulating this recommendation: 1) screening for carotid artery stenosis by ultrasonic Duplex Doppler scanning; 2) screening for cardiovascular risk factors according to recommendations resulting from the Framingham study and other epidemiological studies such as assessing smoking history, lipoproteins such as cholesterol and triglyceride, age, history or diagnosis of diabetes, diet and exercise; 3) using ultrasound B-mode imaging to measure the thickness of the carotid artery "Intima-Media Thickness" (IMT or double line of Pignoli); 4) ECG screening for Atrial Flutter and Atrial Fibrillation; and 5) Transcranial ultrasonic Doppler (TCD) monitoring for emboli from the heart or "paradoxically" from the venous system via Patent Foramen Ovale (PFO).

None of these methods have the sensitivity or specificity to conform to the benefit/cost requirements of an effective screening program. A viable screening program must have an overall cost lower than the cost of the target condition and must result in a reduction in the number of target events to result in an overall cost saving. Each of the considered screening methods will be tested against that standard.

1) Severe Carotid Artery Stenosis does place a patient at risk for atheroembolic stroke. The risk of stroke for a person with a >70% Diameter Reduction stenosis is about 12% in 5 year followup. If that stenosis is treated by endarterectomy surgery or stent intervention, the complication rate of the procedure is about 1% and the 5 year risk of stroke is about 6%, thus, it is necessary to treat 17 severe carotid stenoses to prevent one stroke. There is no method currently accepted to identify the 1/17 stenosis that will rupture and cause a stroke. It is likely that the remaining 6% of patients having stroke even though they have had carotid revascularization also have undiagnosed intracranial stenosis, which cause the stroke even though the carotid stenosis has been successfully treated. The poor predictive value of carotid stenosis has resulted in a quest to identify the stenosis causing atheroma that is vulnerable to rupture.

2) The Framingham Risk Calculator uses a combination of 10 empirically determined historic factors (age over 55, Age adjusted systolic blood pressure, diabetes mellitus, cigarette smoking, prior cardiovascular disease, atrial fibrillation, left ventricular hypertrophy, use of hypertensive medication) to create score along a 30 point scale that predicts the 10 year probability of stroke which ranges from 3% to 84%. Although this might be useful for advisory and actuarial purposes, it does not lead to a definitive intervention. One problem with this method is failure to differentiate between atheroembolic, thromboembolic and hemorrhagic stroke.

3) IMT (Intima-Media Thickness) measurement yielding a thickness >1.7 mm is an empirical indication of increased risk of myocardial infarction. It is not a convincing risk factor for stroke. Although this measurement is moderate in cost, it does not lead to specific intervention but does lead to generalized anti-atherosclerosis treatments including statins and hypertension medications.

4) ECG evaluation for atrial arrhythmia address a separate question of thromboembolic stroke. Although rapid atrial rhythm (Atrial Fibrillation or Atrial Flutter=AF) is considered a risk for stroke, and is treated with anticoagulants for stroke prophylaxis, the culprit atrial mural thrombus, while credible is rarely reported as visualized in the literature. The risk of stroke in the absence of AF increases by only a few percent in the presence of AF (from ~1% to 2%), although the increase in statistically significant when the study numbers are large. One complicating factor in these studies is the overlap between AF, Atrial Septal Aneurysm, Atrial Appendage and Patent Foramen Ovale (PFO). With this overlap, identifying the culprit is not easily accomplished.

5) Transcranial Doppler monitoring for spontaneous thromboemboli from mural thrombus in the heart or from the veins of the legs, crossing from the right to the left heart via a shunt, either Patent Foramen Ovale (PFO) between the atria, an intra-ventricular defect or lung shunt. PFO, a vestige of fetal life) is present in approximately 20% of adults, there is little enthusiasm among physicians to treat PFO with surgical or interventional closure as closure is not believed to be important or effective.

Absent in the evaluation of carotid stenosis is a companion evaluation of the circle of Willis (coW). A disconnected coW is present in 5% of the population. When a disconnected circle of Willis leaving an isolated supply is present, if that supply is compromised by an atheroma causing severe arterial stenosis, the resulting pressure drop across that stenosis combined with the hemodynamic forces that expand the atheroma, make the atheroma vulnerable to rupture.

SUMMARY

Brain swelling (edema), expansion of the cerebral ventricles (hydrocephalus), bleeding into the epidural or subdural spaces (hematoma) and brain tumor are all conditions that compress the arachnoid veins through which blood drains from the skull; this outflow obstruction causes the intracranial pressure (ICP) to increase. The Traditional ICP measurement requires trepanation (drilling a hole in the skull) and placement of a catheter into the brain. The Monro-Kellie Hypothesis of constant intracranial volume requires that on the average, the arterial inflow must equal the venous and cerebrospinal fluid (CSF) outflow from the skull, and within the cardiac cycle, the oscillations of the brainstem and CSF through the foramen magnum must compensate for the pulsatile variations in the arterial supply. This invention uses noninvasive methods to measure the natural pulsations of the thickness of the arachnoid space containing the arachnoid veins (as they accommodate systolic and diastolic flow) and the motions of the brain due to skull acceleration to detect swelling of the brain which compresses the arachnoid veins causing ICP elevation and the associated resultant sequelae.

The decrease in the arachnoid thickness resulting from brain swelling will occur prior to the resulting increase in ICP, thus providing a more sensitive indication of the onset of the treatable pathology.

The disclosed subject matter is a method and instrument to screen asymptomatic people for hypotension in one or more of the six regions of the brain supplied by the corresponding cerebral arteries, which indicates an extreme risk of imminent atheroembolic stroke. Of the three major causes of stroke: hemorrhagic, thromboembolic and atheroembolic; atheroembolism accounts for an estimated 40% of strokes. Atheroembolic stroke can be prevented by in-time application of medical therapy or anatomical intervention by direct surgical or catheter revascularization.

Atheroembolic stroke is caused by the rupture of a vulnerable atheroma along the arterial pathway from the heart to the brain. A vulnerable atheroma causes a pressure reducing stenosis characterized by a pulse delay in the portion of the endorgan supplied by the artery and also a bruit distal to the stenosis. A stenosis results in a pressure drop only if there is no collateral pathway to supply the portion of the endorgan. High blood velocities through the stenosis exceeding 350 cm/s exert combined Bernoulli and Coanda pressure depression on the atheroma exceeding 50 mmHg, promoting neovascular inflation leading to eruption. These high velocities do not cause pressure drop if the downstream expansion to normal size lumen is streamlined avoiding flow separation and allowing laminar flow. Alternatively, if the expansion is sudden, resulting in flow separation, then turbulence in this distal region dissipates energy resulting in pressure drop. Stenotic pressure drop exerts shear stress on the atheroma promoting rupture at the leading edge. These two effects (pressure depression and pressure drop) combine to release atheroemboli from the atheroma which travel to the brain causing stroke and leaving behind an ulcerated crater.

The disclosed subject matter uses noninvasive methods to measure the natural pulsations of the arachnoid space surrounding the brain as the arachnoid veins accommodate systolic and diastolic flow to detect regional cerebral pulse delay to infer the presence of a pressure reducing stenosis in the respective supply arteries. Inside the skull, pulsations in the arachnoid veins are synchronized with the arterial pulsations of the supply arteries in keeping with the Monro-Kellie Hypothesis of constant intracranial volume. The timing of the region specific arachnoid pulsations implicate pulse delays the corresponding specific branch cerebral arteries if these branch arteries have obstructed supply causing local hypotension.

The disclosed subject matter related to methods and apparatus for both noninvasively measuring intracranial pressure, and non-invasively screening for Cerebrovascular Stenosis. The apparatus can include a controller configured to function in the manner described herein to measure or screen for intracranial pressure and/or Cerebrovascular Stenosis. The apparatus can include a headband configured to place a first transducer at a top of a patient's skull and configured to place a second transducer at a lower portion of the patient's skull. Methods for both noninvasively measuring intracranial pressure, and non-invasively screening for Cerebrovascular Stenosis are also disclosed herein.

BRIEF DESCRIPTION OF THE DRAWINGS

The disclosed subject matter of the present application will now be described in more detail with reference to exemplary embodiments of the apparatus and method, given by way of example, and with reference to the accompanying drawings, in which.

DETAILED DESCRIPTION OF EXEMPLARY EMBODIMENTS

A few inventive aspects of the disclosed embodiments are explained in detail below with reference to the various figures. Exemplary embodiments are described to illustrate the disclosed subject matter, not to limit its scope, which is defined by the claims. Those of ordinary skill in the art will recognize a number of equivalent variations of the various features provided in the description that follows.

Figure 1:
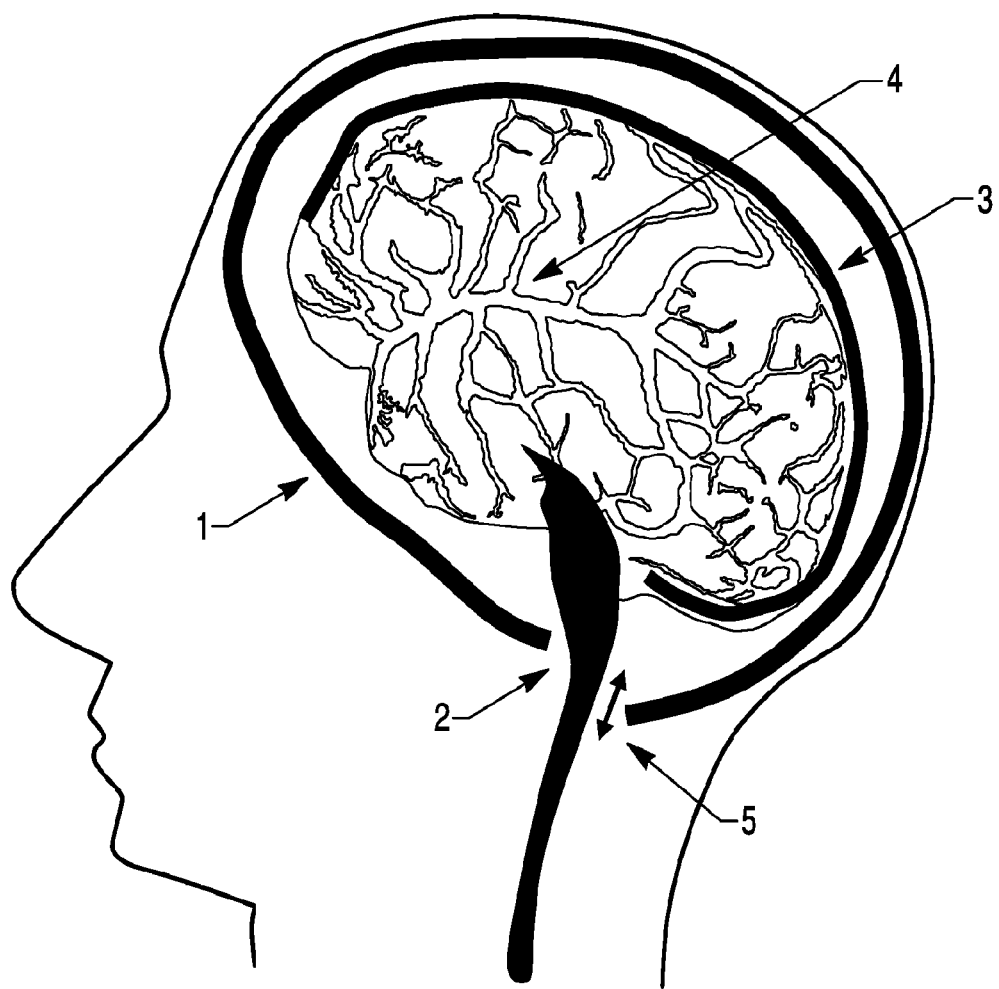
FIG. 1 shows the anatomy of the skull and brain in sagittal section.

FIG. 1 illustrates the anatomy of the human skull and brain in sagittal section. The skull 1, houses the foramen magnum with brainstem passing through 2, superior sagittal venous sinus 3, arachnoid venous web covering the surface of the brain 4, and the CSF pulsations 5 in and out of the skull 1.

Figure 2:
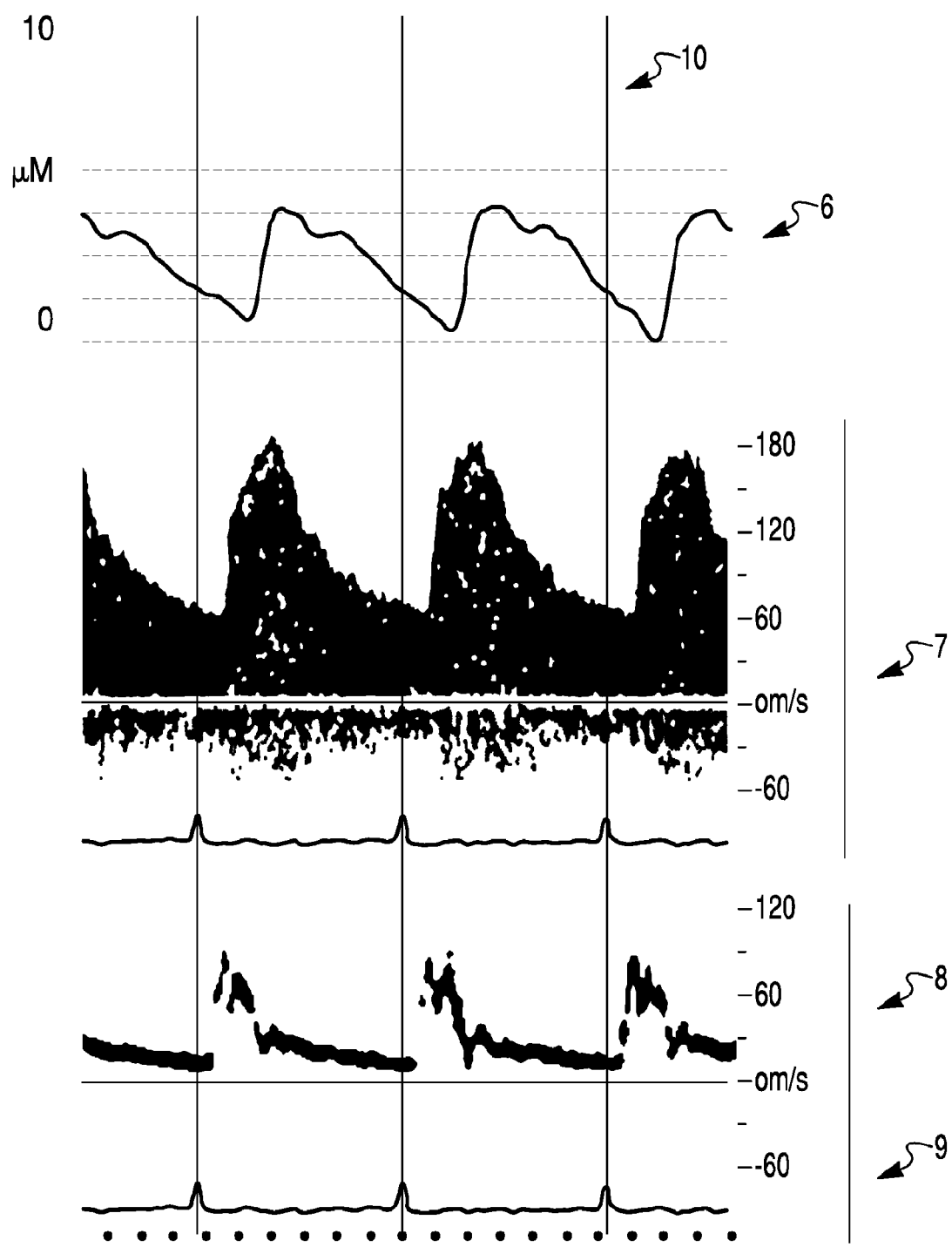
FIG. 2 shows measurement from a person showing waveforms of 3 cardiac cycles.

FIG. 2 shows a graphical measurement from a person showing waveforms of 3 cardiac cycles.

Zone 6 of FIG. 2 shows the motion of the brain away from the skull during systole, Zone 6 of FIG. 2 shows the Middle Cerebral Artery Velocity Spectral Waveform showing the velocity waveform of blood entering the brain. Zone 8 of FIG. 2 shows the Common Carotid Artery Velocity Spectral Waveform showing the velocity of blood ascending through the neck. Zone 9 of FIG. 2 shows the ECG for QRS timing, Zone 10 of FIG. 2 shows vertical lines depicting QRS timing.

According to the Monro-Kellie hypothesis, the flow of materials into and out of the constant volume cranial vault shown in FIG. 1 must be equal, moment to moment. Pulsatile arterial inflow delivers 10 ml of blood during the first half of the cardiac cycle plus 5 ml during the remaining half of the cycle shown in zone 7 of FIG. 2, via the internal carotid and basilar arteries; venous outflow via the jugular foramen must be equal. In compensation for the input pulsation, Cerebral Spinal Fluid (CSF) and brainstem pulsate through the foramen magnum (cross section 0.76 sqcm) the systolic 0.2 ml CSF outflow returns in diastole accompanied by the 0.1 mm systolic descent of the brainstem which also returns during diastole.

Part of the systolic excess of blood is temporarily stored in the web of arachnoid veins that surround the cortical surface of the brain, separating the brain from the interior surface of the skull. These flaccid veins inflate, becoming more circular in cross section, expanding the thickness of the 600 sqcm arachnoid space about 5 μm in systole as shown in zone 6 of FIG. 2. The waveform of the arachnoid space caused by the pulsation of the arachnoid veins mimics the arteriolar waveforms seen in parts of the body that are free to expand. The effect is local to the cerebral region, and thus serves as a method to analyze the waveform of the corresponding branch cerebral artery. Waveform features including pulse delay and morphology can be analyzed.

Figure 3:
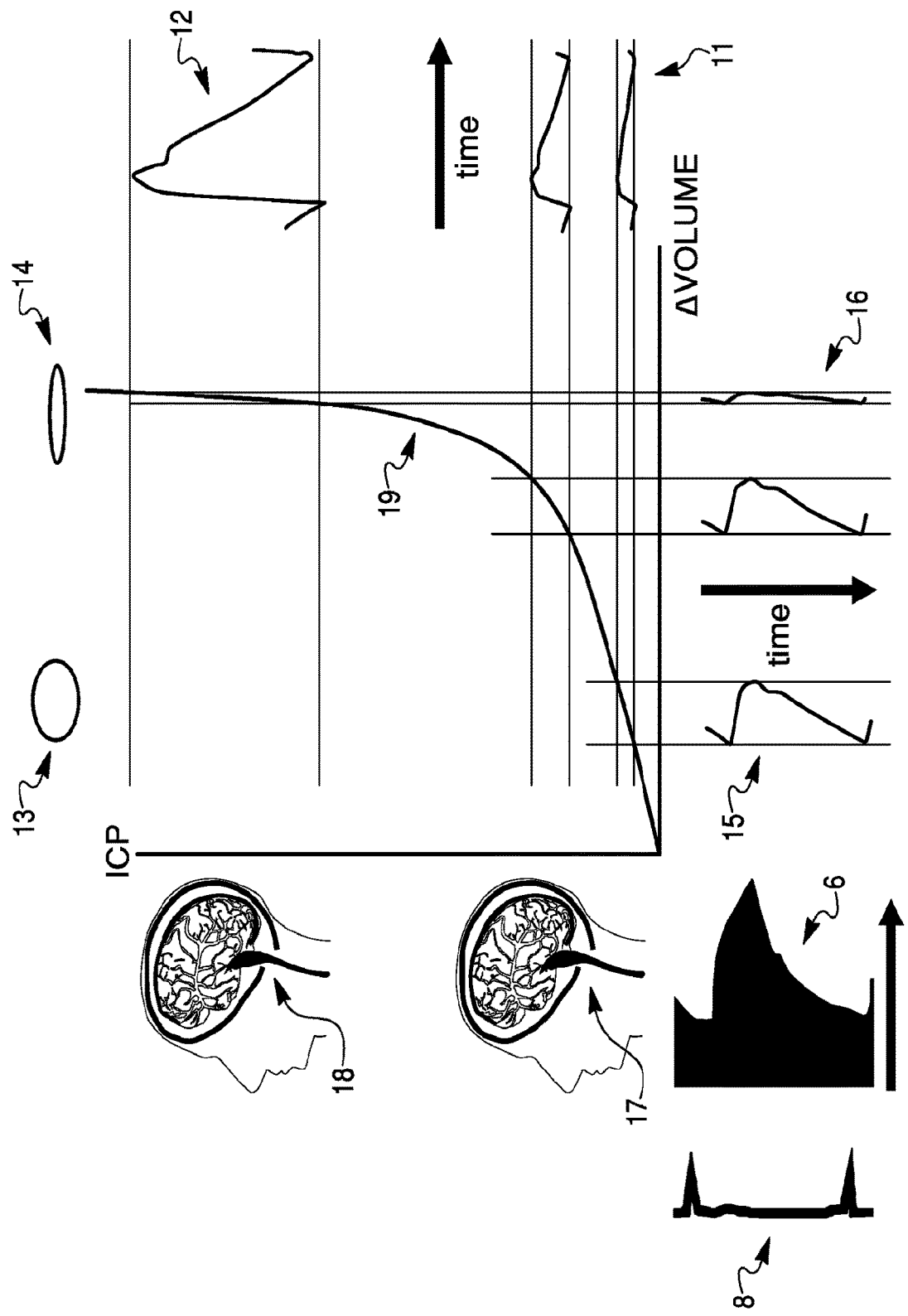
FIG. 3 shows the compliance curve of the brain volume within the skull.

FIG. 3 shows the compliance curve of the brain volume within the skull. Intracranial Pressure (ICP) is graphed vs. increase in volume of brain and blood in the skull excluding the portion of the CSF and brainstem that pulsates through the foramen magnum {ΔVOLUME}. Zone 11 of FIG. 3 shows normal ICP pressure pulsations with the cardiac cycle. Zone 12 shows excessive ICP pressure pulsations. Zone 13 shows partially inflated arachnoid vein cross section with low blood outflow resistance. Zone 14 shows a compressed arachnoid vein cross section causing high blood outflow resistance. Zone 15 of FIG. 3 shows normal arachnoid vein volume pulsations. Zone 16 shows diminished arachnoid vein pulsations with increased ICP and reduced compliance. Zone 17 shows normal brain and brainstem position with brainstem and CSF free to move elastically in and out of the skull. Zone 18 shows expanded solid brain tissue in skull with brainstem wedged in the foramen magnum restricting motion of brainstem and CSF. Zone 19 shows a compliance curve showing change in ICP with change in injected fluid volume.

If the normal brain were not perfused with blood, then the Intracranial pressure {ICP} would be near zero at the axis origin, as shown in FIG. 3. The compliance curve 19 extends from that origin with increasing slope as volume is added to the brain volume including brain tissue swelling (edema), tumor, hematoma, and confined CSF in the four ventricular spaces of the brain and the arachnoid space around the brain. Expanding brain volume: 1) reduces the thickness of the arachnoid space flattening the arachnoid outflow veins and 2) expels mobile brainstem and mobile CSF through the foramen magnum. These mechanisms are limited: the arachnoid space contains a limited volume of venous blood and mobile CSF (200 cc); the brainstem has limited elastic mobility. It is the high or low outflow resistance of the arachnoid veins resulting from the degree of cross section compression 14 that ultimately determines intracranial pressure because the terminal intracranial great venous sinuses are tethered open to the jugular foramen where they exit the skull, and if elevated above the right atrium of the heart are at atmospheric pressure.

ICP=(Brain Flow Rate)*(outflow resistance)

The normal thickness of the arachnoid space is 3 mm. The resistance of the arachnoid veins increases: by 5 fold if the space is compressed to 1 mm, by 12 fold if the space is compressed to 0.5 mm and by 90 fold when compressed to 0.25 mm. Thus, the onset of increased ICP is very sensitive to arachnoid space thickness determined by brain volume expansion.

The normal 3 mm thickness of the arachnoid space increases with age and dementia to nearly 10 mm at age 100. Thus the elder brain has increased tolerance to temporary brain volume expansion.

Figure 4:
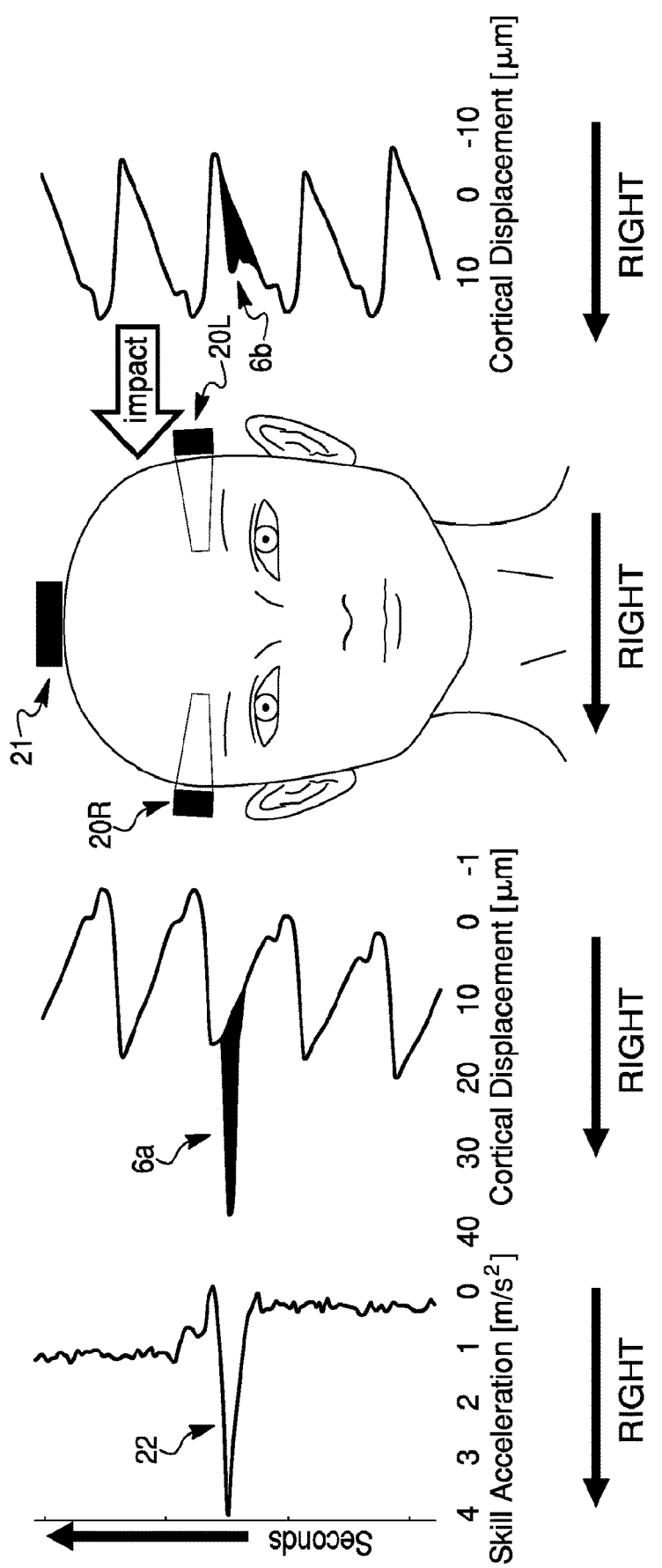
FIG. 4 shows measurement from a person showing brain motion due to mild head impact.

FIG. 4 shows measurement from a person showing brain motion due to mild head impact on the left.

In FIG. 4, zone 6a shows the motion of the brain away from the skull during systole and motion toward the skull (toward the right) during right acceleration. Zone 6b shows the motion of the brain away from the skull during systole and motion away from the skull (toward the right) during right acceleration. A right temporal transducer 20R, a left temporal transducer 20L, and an accelerometer 21 can be attached to the skull as shown in FIG. 4. Zone 22 shows the acceleration of the skull including impact pushing skull to the right.

It is unexpected that the brain moves to the right when the skull is accelerated to the right as shown in FIG. 4. This is due to the buoyancy of the brain in the surrounding arachnoid fluids. Brain density is 1.03 gm/cc, CSF density is 1.01 gm/cc, and blood density is 1.05 gm/cc. Although the blood has direct communication between the right and left through the superior sagittal venous sinus (FIG. 5 (3)) and other conduits, the lateral motion of the CSF is impeded by the falx cerebri 24 which provides a partition between the left and right cerebral hemispheres. Thus the brain dynamics are primarily affected by "floating" in the contained venous blood rather than sinking in the CSF.

Behavior of the arachnoid veins also dominates elevation of ICP; compressed arachnoid veins with high flow resistance require high supply pressure (high ICP) to accommodate normal perfusion flow rates through the brain. According to an approximation of the Poiseuille law for laminar flow in an elliptical conduit (like the compressed arachnoid veins), the pressure drop increased by the inverse third power of the arachnoid thickness for elliptical short axis dimensions below 1 mm (corresponding to an elliptical axis ratio of 2); thus a decrease in the arachnoid thickness pulse amplitude indicates a nonlinear increase in the ICP due to arachnoid vein outflow obstruction.

Because the arachnoid veins drain the local region of the cortex, the flow obstruction is regional rather than global. Pulsation amplitude and waveform of the arachnoid thickness provides a local index to the ICP and brain cortex perfusion.

Figure 5:
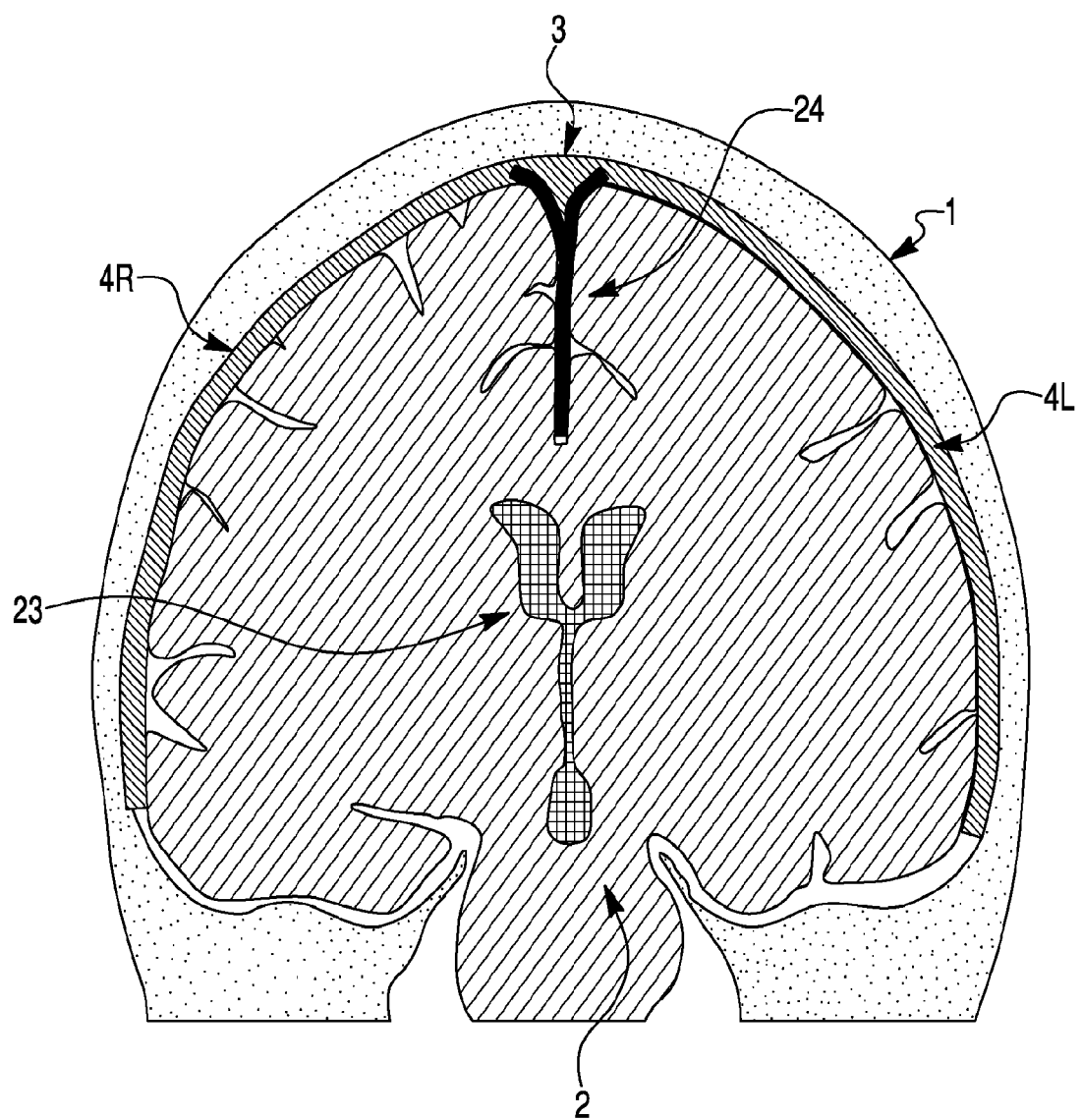
FIG. 5 shows a frontal cross section through a human skull.

FIG. 5 shows a frontal section through the human skull 1, depicting the foramen magnum with brainstem passing through 2, the superior sagittal venous sinus 3 providing a direct connection between the right arachnoid venous web and the left arachnoid venous web, the left arachnoid venous web 4L covering the surface of the left hemisphere of the brain, the right arachnoid venous web 4R covering the surface of the brain, and cerebral ventricles 23 containing CSF.

Figure 6:
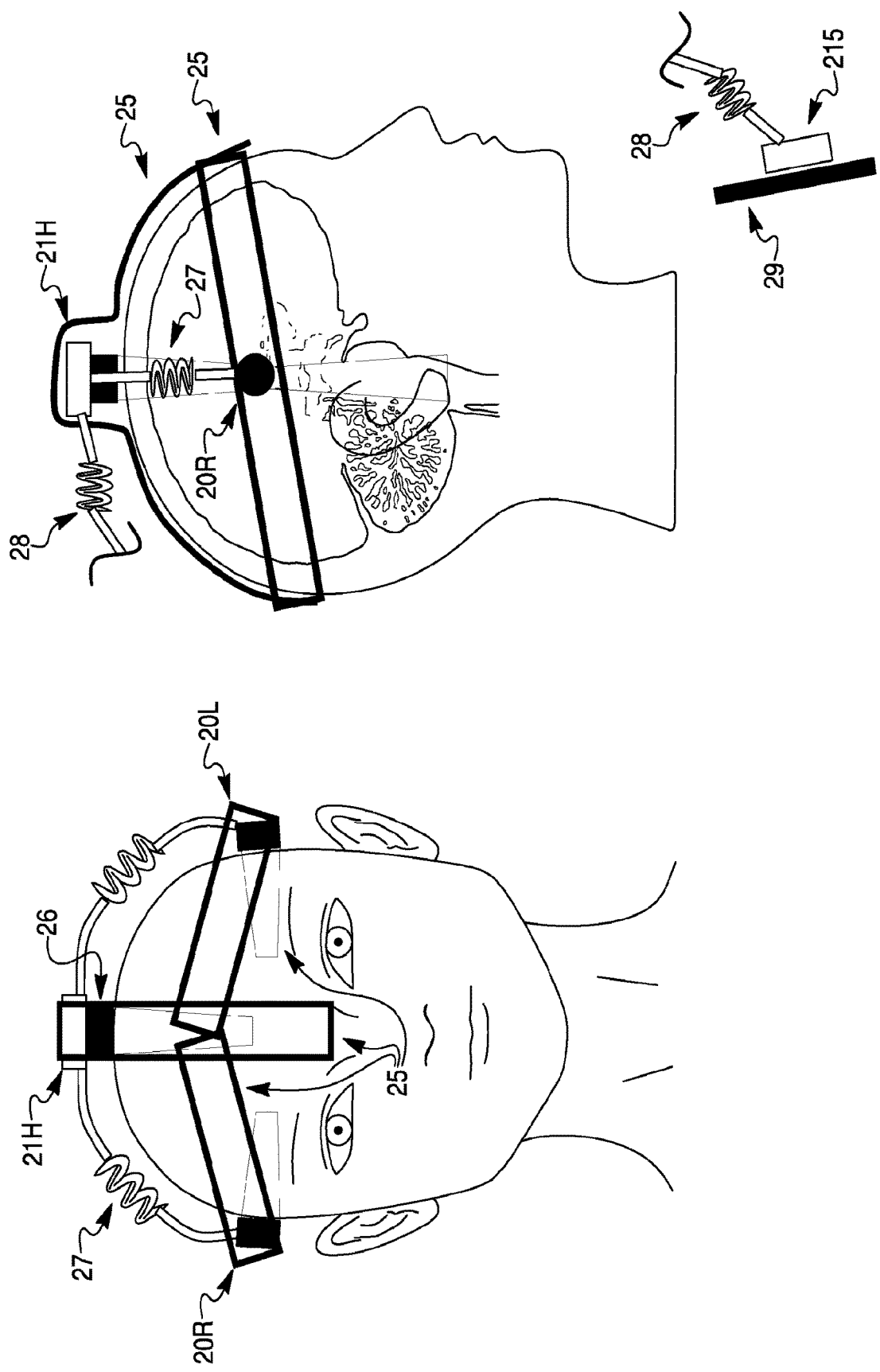
FIG. 6 shows a transducer configuration in accordance with an embodiment of the presently disclosed subject matter.

In one embodiment, the system can include or consist of a device to measure the pulsations in the thickness of the arachnoid space and other cranial structures to identify the characteristic waveforms of increased ICP. FIG. 6 shows an arrangement of 3 brain motion transducers 20R, 20L and 26, the lateral transducers each measuring the pulsatile motion of the adjacent cortical tissue and the superior transducer measuring the motions of the brainstem and/or the flow of CSF. An accelerometer 21H secured to the skull monitors skull acceleration that will affect cortical motions. The superior accelerometer 21H and an associated sternal accelerometer 21S together provide information to estimate the elevation between the right atrium of the heart and the cranial vault.

Figure 7:
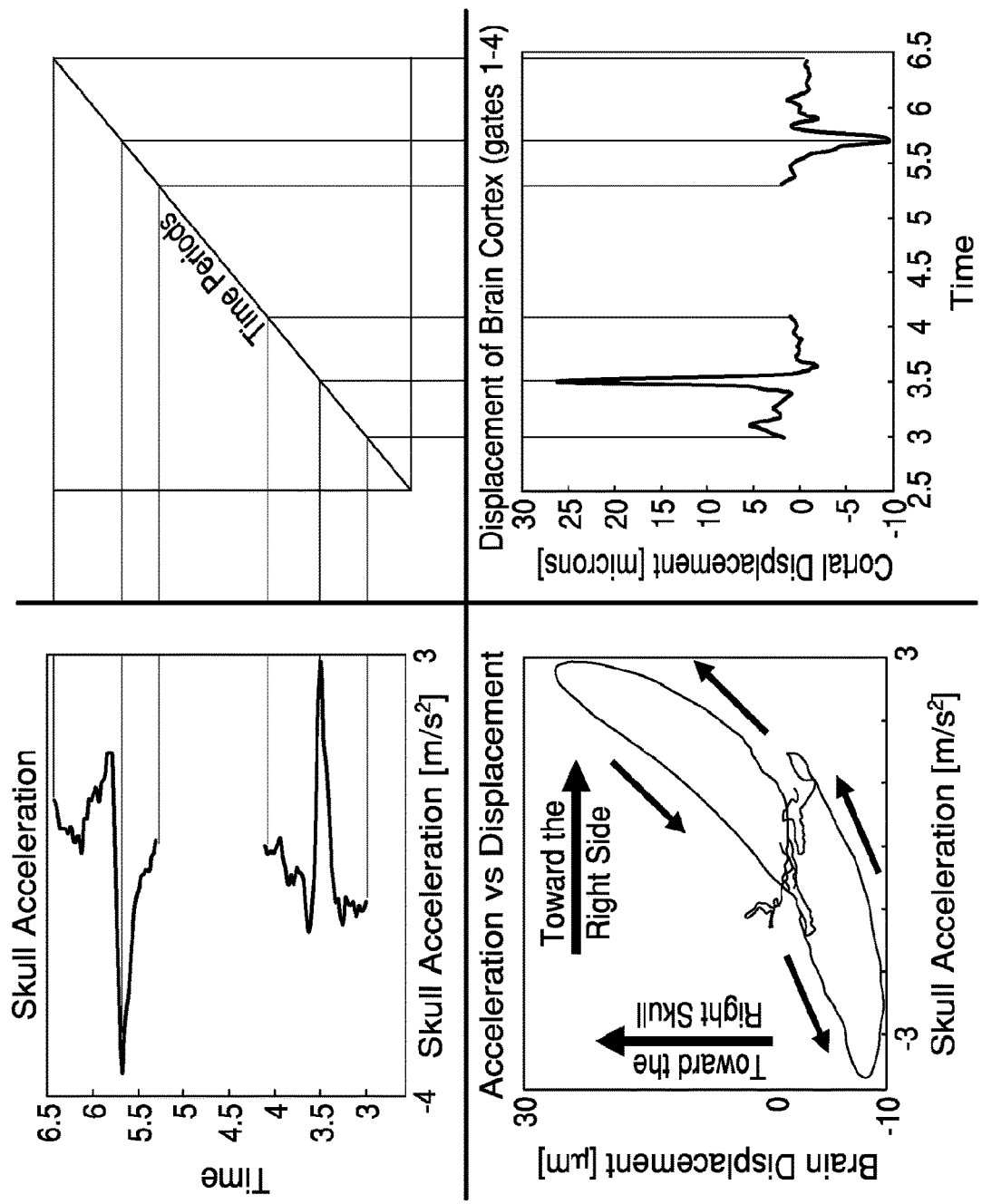
FIG. 7 shows a Lissajous figure of skull acceleration and brain motion.

In one embodiment, the system uses arachnoid thickness motion measurements from left and right lateral transducers 20L & 20R in association with the measurements of lateral motion from a head accelerometer 21H, taking the difference between the arachnoid thickness measurements to show lateral brain motion, and associating this motion with the acceleration to determine the dynamic characteristics of the brain such as the natural oscillation frequency, amplitude of motion, and oscillation damping, as shown in FIG. 7.

In one embodiment, reusable transducers are attached to the scalp skin of the head in a way that minimizes motion between the transducer and skull during the measurement.

Figure 8:
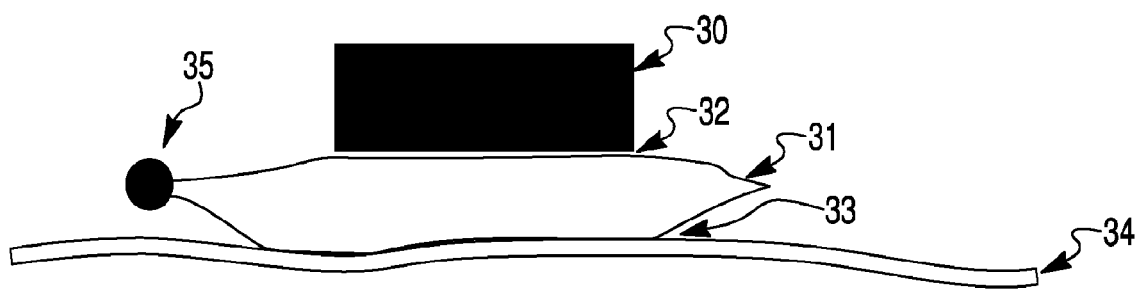
FIG. 8 shows a transducer skin contact gel pad.

This allows the exchange of signals between the transducer, skull and brain, provides for sanitary conditions, while permitting easy and safe removal from fragile skin. This can be accomplished with a disposable gel pad as shown in FIG. 8 consisting of or including an envelope containing a thin layer of viscous gel 31, excluding gas or air with a superficial adhesive 32 with removable adhesive protection. The exposed adhesive will attach and conform to the shape of the transducer face, with a biological compatible adhesive 33 on the face with removable protection. The exposed adhesive will attach and conform to the undulating shape of the patient skin. After use, to facilitate easy removal from fragile skin, a zip-tear 35 on the exposed edge of the envelope 31 is removed, allowing air to enter the envelope, allowing independent deformation of the skin envelope surface from the transducer envelope surface, so that the gel pad can be easily and safely removed.

The transducer device of FIG. 8 can include a transducer 30, a flat pouch 31 filled with a thin layer of viscous fluid, an adhesive surface 32 for transducer attachment, an adhesive surface 33 for contact with skin 34, and a zip vacuum release 35.

Figure 9:
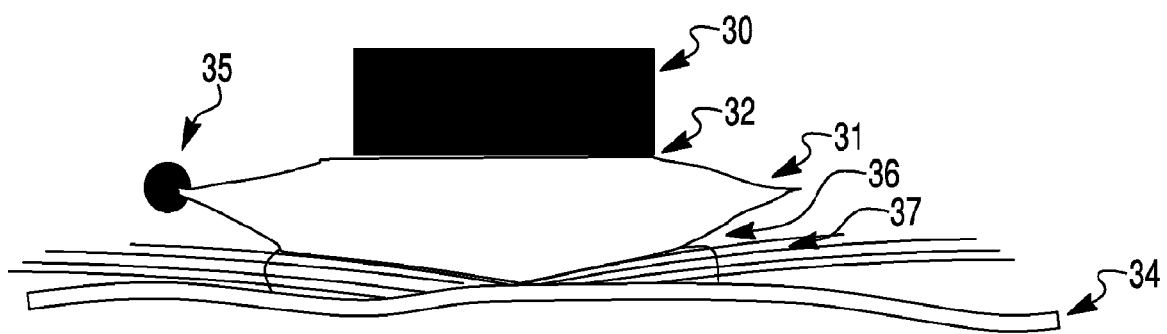
FIG. 9 shows a transducer scalp hair contact gel pad with adhesive gel.

In another embodiment, reusable transducers are attached to the hair over scalp of the head in a way that minimized motion between the transducer and skull during the measurement. This allows the exchange of signals between the transducer, skull and brain, provides for sanitary conditions and allows easy and safe removal from hair and fragile skin. Attachment through the hair can be accomplished with a disposable gel pad (FIG. 9) consisting of an envelope containing a thin layer of viscous gel, excluding gas or air 31 with a superficial adhesive 32 with removable adhesive protection; the exposed adhesive will attach and conform to the shape of the transducer face, with a biological compatible adhesive hair penetrating gel 36 on the face with removable protection; after parting the hair the exposed adhesive will attach and conform to the undulating shape of the hair and scalp, the adhesive gel penetrating the hair and excluding entrapped hair. After use, to facilitate easy removal from fragile scalp, a zip-tear 35 on the exposed edge of the envelope 31 is removed, allowing air to enter the envelope, allowing independent deformation of the skin envelope surface from the transducer envelope surface, so that the gel pad can be easily and safely removed.

In all embodiments of the display for patients or medical personnel, the display includes a binary result indicating that one or more signals are corrupt. One source of corruption in ultrasound examination is obstruction of the ultrasound beam by air in the ultrasound beam path. Such air might be present in the contact zones between the ultrasound transducer and the patient tissues. Such air might be present inside internal voids such as the air filled sinus in the frontal bone of the skull. In one embodiment of the display for patients or medical personnel, the display shows a binary result indicating that the measurements are either consistent with normal ICP or with elevated ICP. In another embodiment of the display, one or a combination of the following are shown: 1) numeric values for arachnoid space thickness pulse amplitude, 2) numeric values for the slope relationship between skull acceleration and brain displacement, 3) numeric values or graphical display indicating the phase relationship between the skull acceleration and the brain displacement, 4) numeric or graphical values indicating the waveshape or timing of the brain pulsations, 5) numeric or graphical values comparing the amplitude and waveshape of the arachnoid space thickness pulsations with the amplitude and waveshape of the brainstem pulsations. In an enhancement of the display information, data regarding the relative elevation of the cranial vault from the right atrium ascertained from the measurements of the sternal accelerometer and the cranial accelerometer is included in the display or in the computations resulting in a display.

Assuming that the volume of blood entering the skull during systole is constant because the arterial blood pressure is much higher than the IntraCranial Pressure (ICP), the brainstem will have a greater pulsatile motion during normal ICP (greater compliance) and smaller pulsatile motion during higher ICP. An explanation is provided by examining the anatomy of the brainstem. The brainstem is a conical structure with larger diameter cephalad. During periods of lower ICP, the brainstem is retracted into the cranium, but during periods of higher ICP, the brainstem is advanced into the Foramen Magnum, and the larger conical diameter restricts motion.

The pulsatile motion of the brainstem can be motored with Tissue Doppler with an ultrasound transducer located on the posterior of the neck with the ultrasound beam directed through the Foramen Magnum or alternatively an ultrasound transducer on the top of the skull directed downward through the Foramen Magnum. In either case, the range gates of the transducer should be set to 10 or 12 cm. Of the two locations, the most stable is the superior location, as the alignment will not be affected by motions of the head that flex the neck. An associate accelerometer provides the head orientation, and coupled with an accelerometer on the sternum and the assumption of a fixed length of the neck, complete information about the elevation of the skull from the heart is available.

If the brain swells it fills space and obliterates open areas in the skull. The ultrasound system should be configured to detect both pulsatile motion at the heart rate and harmonics and vibrational information. Tissue vibrations might occur during periods of elevated intracranial pressure as both CSF and venous blood pass through narrowed passages causing turbulence. Such turbulence is observed during urination in the presence of urethral stenosis due to prostatic hypertrophy, during arterial blood flow through atherosclerotic stenoses, during blood flow through valvular stenoses.

Embolic strokes occur when an artery supplying a portion of the brain is occluded (no blood flow). Most often, occlusion occurs when an embolus blocks a branch artery inside the skull. The normal lumen cross-section of an artery decreases with each bifurcation; occlusion occurs when the size of the embolus is greater than the distal lumen. In the normal branching arterial tree, the lumen diameter is proportional to peak systolic flow; the normal evolving artery increases in diameter until large enough to avoid turbulence even at the highest flow rate. At each branch point, the daughter artery diameters are smaller than the parent artery. Thus, a solid embolus will travel along the branching arterial tree toward the endorgan with diminishing cross-section until the embolus matches the lumen size and becomes an occluding plug.

Thromboemboli originate from several sources proximal to the aortic valve: an infarcted left ventricle of the heart, a fibrillating left atrium of the heart, or "paradoxically" via a right-to-left shunt in the heart from a thrombosed vein. Such thromboemboli can travel to any endorgan in the body, about 10% are likely to go toward the brain causing a stroke. Such fibrin rich thromboemboli are amenable to dissolution by tissue Plasminogen Activator (tPA). Atheroemboli originate from the eruption of a stenotic atheroma originate from the arteries between the heart and the endorgan leaving ulceration in the arterial wall marking the atherosclerotic location. These atheromas when sufficiently large cause stenosis in the artery and if collateral bypass pathways are absent, three hydraulic forces act to disrupt the atheroma: 1) Bernoulli and 2) Coanda effects cause pressure depression at the atheroma promoting internal hemorrhage in the atheroma and atheroma expansion, thus increasing the severity of the stenosis, and 3) pressure drop causes shear at the base of the atheroma tending to rend the proximal margins of the lesion. Eruption releases atheroemboli comprised of contained lipids and cellular debris that travel along the branching arterial tree toward the endorgan with diminishing cross-section until the embolus matches the lumen size and becomes an occluding plug. Atheroemboli are not amenable to dissolution by tPA. Overall, about half of cerebral embolic occlusions are successfully lysed, either completely or partially with tPA suggesting that half of the emobli are fibrin rich thromboemboli and the other half are atheroemboli. After the original atheroma eruption, the residual ulceration is thought to be favorable to the formation of platelet rich thrombi which can cause subsequent thromboembolic events, but these platelet rich thrombi, originating from an atherosclerotic ulceration are resistant to dissolution by tPA. This invention is not intended to detect these secondary ulceration source thromboemboli, as these thrombi are not likely to cause pressure reducing arterial stenosis; this invention is intended to detect only primary pressure reducing stenoses caused by atheroma, which are at risk of rupture.

The disclosed subject matter is based on the conclusion that 250,000 US strokes per year are primary atheroembolic strokes originating from a pressure reducing stenosis between the aortic valve and the brain and that if detected on screening, the majority can be successfully treated medically and the success of such treatment can be easily monitored to triage medical treatment failures to surgical intervention, thus eliminating cerebrovascular atherosclerosis as a cause of stroke.

Because severe extracranial and intracranial atherosclerotic stenosis is expected in only 1/500 people over the age of 50 (and in fewer under the age of 50), the screening method is designed to cost less than an electrocardiogram examination and near the cost of a blood pressure measurement.

The savings for each stroke prevented is estimated at $40,000 US, the cost of screening 500 people is estimated at $5,000 US.

The pulse waveform in an artery distal to a pressure reducing stenosis is characterized by a pulse delay. If the stenosis is located at the origin of the internal carotid artery and, in addition, the patient does not have collateral supply via the coW, a pulse delay is present in the ipsilateral eye and also in the associated regions of the cortex. The pulse delay in the eye has been demonstrated in such cases, showing that eye pulse delay was predictive of stroke with sensitivity and specificity equivalent to the other methods available. However, this technique is sensitive to pressure reducing stenoses in the Internal Carotid Artery (ICA) and Ophthalmic Artery (OA); in contrast, pulse delay in the brain offers the promise of identifying pressure reducing stenoses in the ICA, MCA, ACA, PCA caused by atheroma that is vulnerable to rupture.

Only 50% of people have complete coW, which can provide collateral compensating blood flow in the case of a carotid stenosis. An additional 45% have one segment of the coW missing such as the Posterior communicating Artery (PcomA) 17, which also provides collateral flow. The remaining 5% have two segments missing, often the Anterior communicating Artery (AcomA) 16 and PcomA. This latter condition is called a disconnected circle of Willis (coW). With a disconnected coW, if the ipsilateral carotid artery has a pressure reducing stenosis, the eye and the ipsilateral lateral and frontal segments of the brain will have pulse delay and regional hypotension. Although the measurement of the eye pulse delay (OPG test) can indicate an uncompensated carotid artery stenosis, a stenosis of the ophthalmic artery can also cause ocular pulse delay, resulting in a false positive test. By combining the OPG with carotid bruit detection in the neck, it is possible to match the predictive value of conventional carotid ultrasonic duplex Doppler scanning for stroke from a carotid stenosis due to an atheroma vulnerable to rupture which could be treated with endarterectomy, stent or medical therapy.

If a pressure reducing stenosis is present in the branch arteries above the coW, the patient will have cerebral regional hypotension which is marked by cerebral pulse delay and bruit near the coW. There is presently no diagnostic method in use for this condition.

Because the arachnoid veins drain the local region of the cerebral cortex, the pulsation amplitude and waveform of the arachnoid thickness provides a local index to the pulse of the respective supply artery. Delayed arterial pulse arrival results in delays in the local arachnoid thickness waveform over the cerebral region supplied. Thus, a local delay in the arachnoid thickness waveform indicates a pressure reducing stenosis somewhere along the arterial supply pathway. The location of the pressure reducing stenosis can be identified by utilizing microphone or ultrasound beam to locate the vibration indicating a pressure reducing stenosis.

Figure 11:
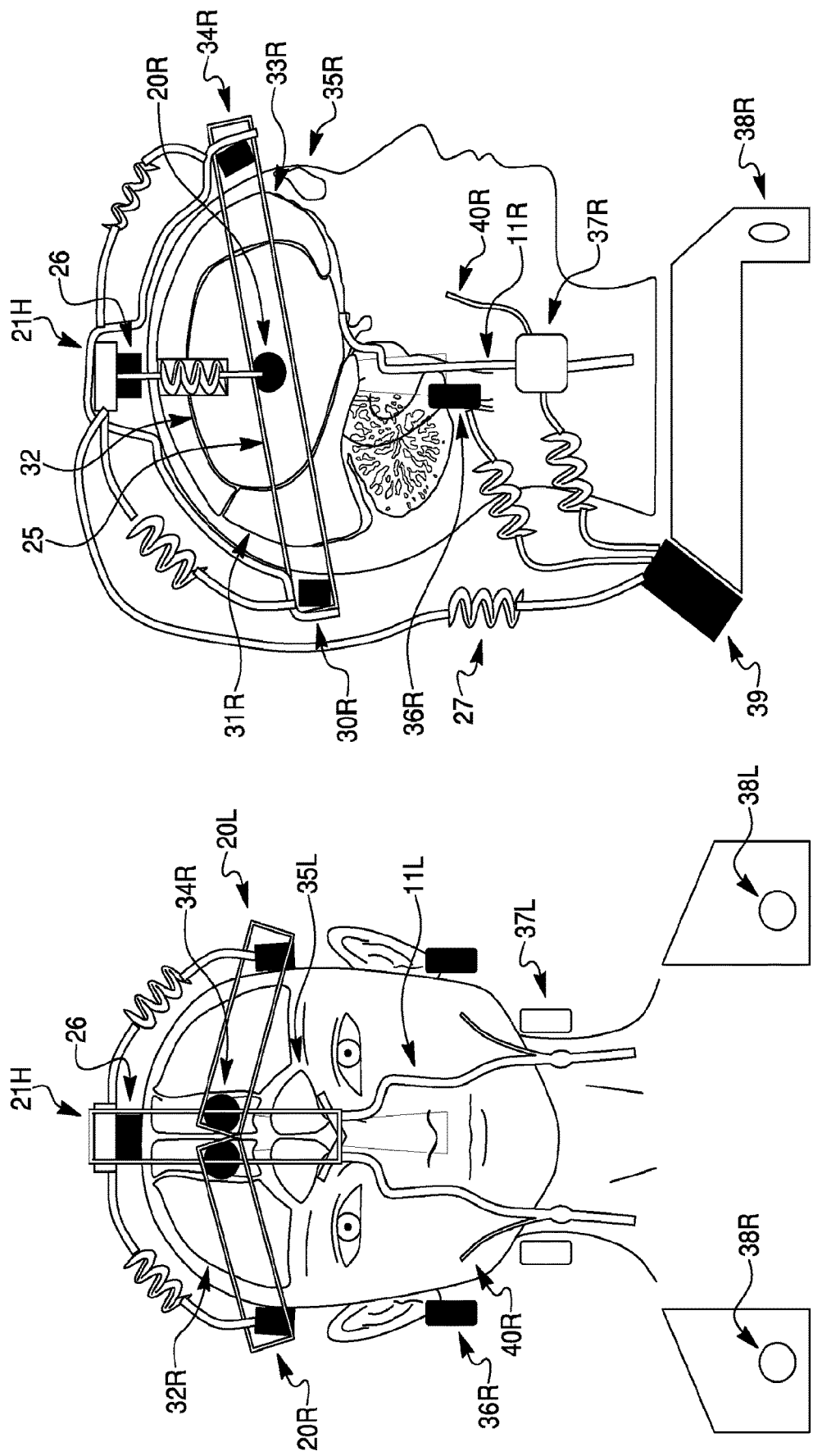
FIG. 11 shows a transducer configuration according to another embodiment of the presently disclosed subject matter.

In one embodiment, the system of the presently disclosed subject matter consists of or includes a device to measure the pulsations in the thickness of the arachnoid space corresponding to each of the six perfused region of the brain to identify the pulse delay characteristic of regional cerebral hypotension indicating that there is a pressure reducing stenosis in the pathway between the heart and the corresponding region of the brain. FIG. 11 shows an arrangement of 7 brain motion transducers marked as 20R, 20L, 30R, 34R, 26, plus two unlabeled, each of the circumferential transducers measuring the pulsatile motion of the adjacent cortical tissue; the superior transducer 26 measuring the motions of the brainstem and/or the flow of CSF through the foramen magnum. An accelerometer 21H secured to the skull monitors skull acceleration that will affect cortical motions.

The carotid bifurcation phonoangiography microphones 37 provide additional diagnostic information. In addition to causing a pulse delay in the endorgan supplied by a pressure reducing stenosis, a pressure reducing stenosis also is characterized by a bruit emitting from the region of post-stenotic turbulence. In the presence of a regional cerebral pulse delay which includes the MCA distribution 32, an ipsilateral carotid bruit confirms the presence of a pressure reducing stenosis in the proximal ICA. Because of the high hemodynamic forces on the atheroma (Bernoulli, Coanda, and pressure drop shear), the atheroma is likely to rupture leading to atheroembolic stroke in some portion of the hypotensive region. Current medical practice recommends therapy such as carotid endarterectomy, carotid stenting or aggressive anti-atherosclerotic medical therapy. In the presence of a cerebral pulse delay, but absence of a carotid bruit, the pressure reducing stenosis is likely present inside the skull near the coW. In that case, a bruit will be emitted from that post-stenotic turbulence. Such a bruit can be detected by implementing certain processes which can be implemented from the skull transducers 20, P26, 30, and 34.

At present, interventional treatments for intracranial stenosis are experimental, but aggressive medical therapy is effective. Patients with regional cerebral hypotension and bruit, if treated medically, can be followed for improvement of the cerebral perfusion pressure to verify that the treatment was effective in eliminating the stenosis.

The ear photoplethysmograph transducers 36 provide additional diagnostic information. Kartchner and McRae have shown that an ear pulse delay indicates stenosis in the ipsilateral external carotid artery or a branch thereof. The ear pulse waveform provides a model of the patient specific waveform which can be used in signal processing for each of the cerebral regions to establish the pulse delay. Because of the possibility of external carotid artery stenosis causing an ear pulse delay in one ear, waveforms from both ears should be gathered and the earlier waveform should be used for analysis. Because if the slim possibility of bilateral external carotid stenosis, the ear pulse should be compared to the ECG QRS cardiac timing to rule out bilateral external carotid stenosis.

Dual optical wavelength ear photoplethysmograph signals can be used to perform ear pulse-oximetry. Including ear oximetry in the examination provides an important additional diagnostic tool for identifying patients with Patent Foramen Ovale of the heart which is thought to be a cause of thromboembolic stroke. The measurement of ear oxygen saturation decrease after a Valsalva maneuver has a sensitivity of 85% and specificity of 100%. Although the interventional closure of PFO is controversial, patients with PFO can be advised to use prophylaxis methods in situations when venous thrombosis due to stasis or hyper-coagulation is more likely such as during travel, pregnancy, certain prescription use or hospitalization. Prophylaxis methods include: wearing venous compression stockings or using prescription anticoagulation The key diagnostic information for identifying the presence and location of pressure reducing cerebrovascular stenosis is contained in one style of exemplary display.

Figure 10A:
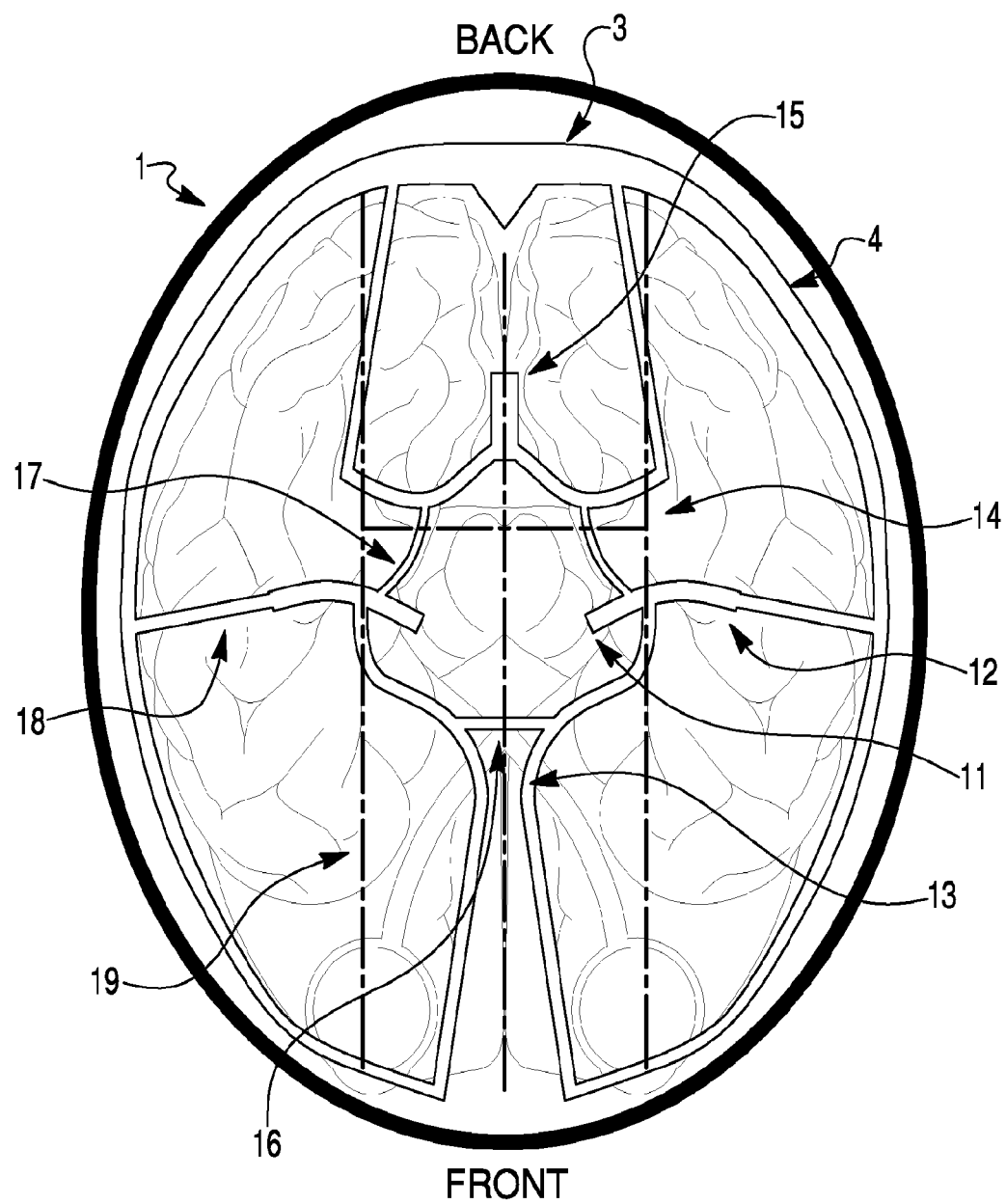
FIG. 10A shows radial circulation of blood in a human skull.
Figure 10B:
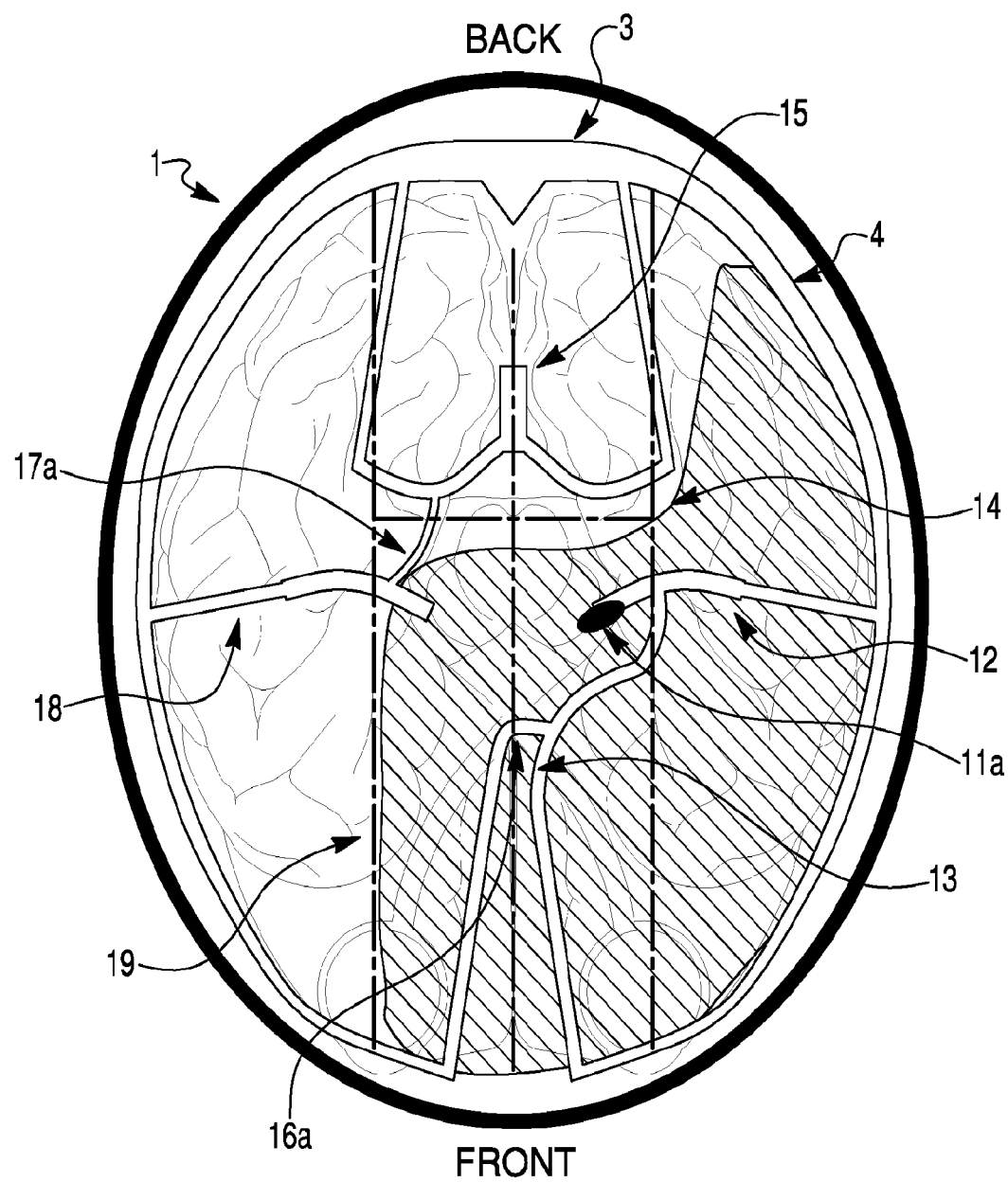
FIG. 10B shows a disconnected Circle of Willis in a human skull.
Figure 12:
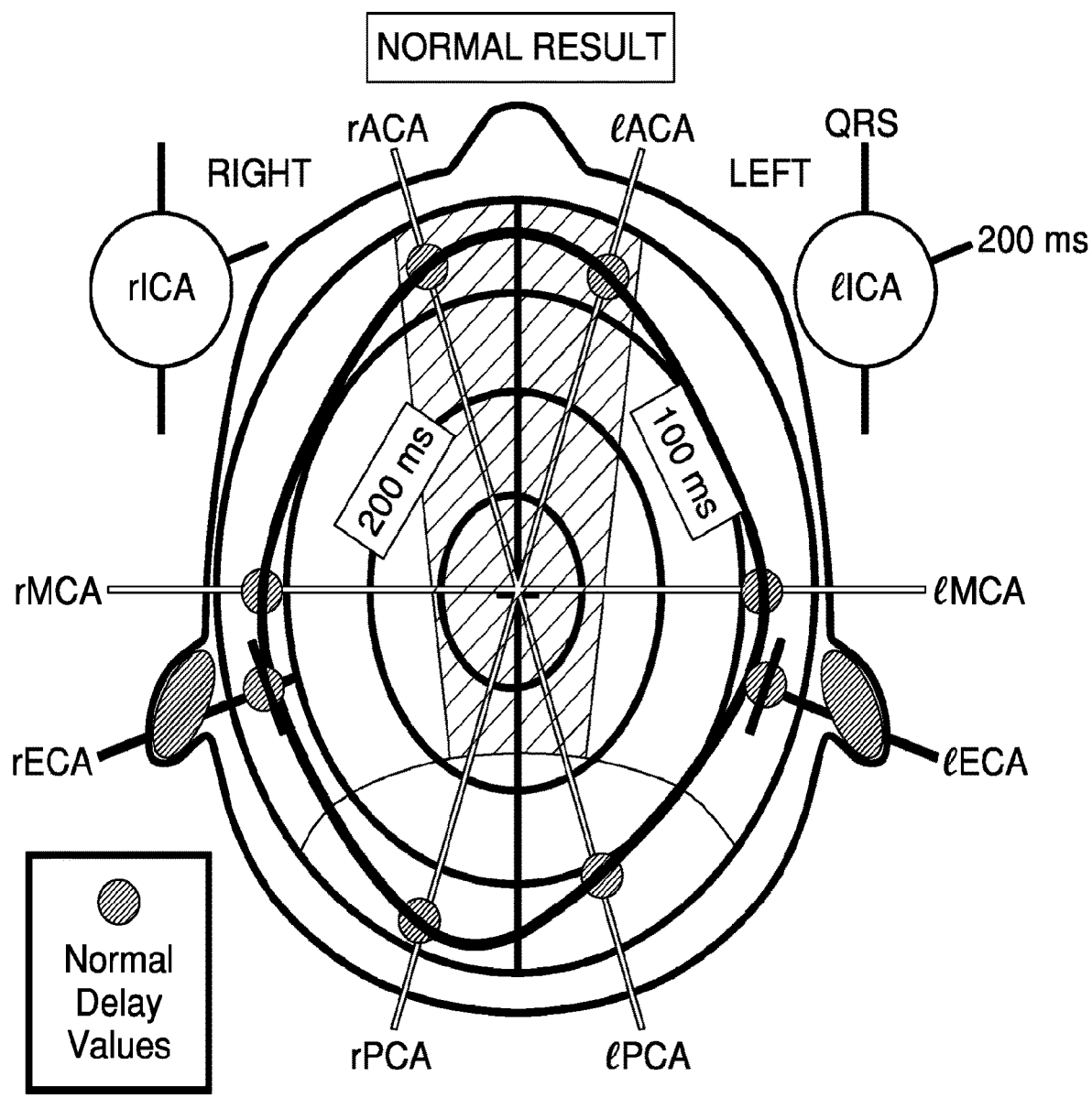
FIG. 12 shows a normal examination report for pulse delay.
Figure 13:
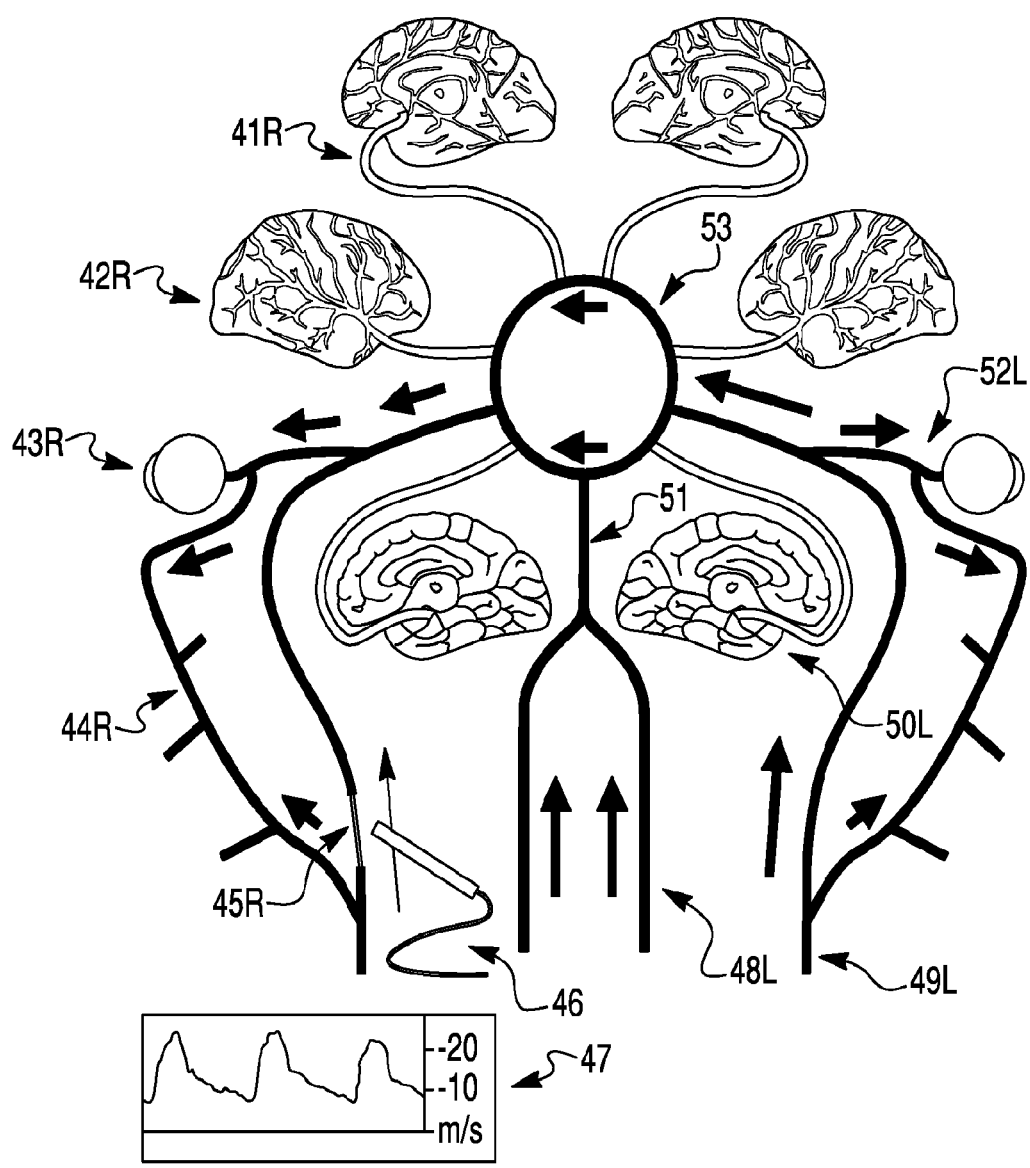
FIG. 13 is a cardiovascular circuit diagram.

FIG. 12 shows an exemplary report display for a normal patient. Underlying the display is an arterial distribution map of the brain overlaid with elliptical contours indicating the pulse delay measured in each artery: 0 millisecond (ms), 100 ms, 200 ms and 300 ms with the center point indicating 400 ms pulse onset delay after ECG-QRS. The patient specific delay plot intersects six radial lines, each corresponding to the branch artery specific pulse delay with an icon circle each indicating the values from the individual transducers. Additional circle icons mark the normal ear pulse delays. All normal delays are <100 ms. Icons for indicating carotid bruits adjacent to the neck on the left and right show no bruit detected FIG. 13 shows the cerebrovascular arterial circuit diagram for a classic patient with a flow reducing stenosis on the right ICA. The circle of Willis is complete, as in 50% of people. Potential collateral pathways via the ECA (passing via the Ophthalmic Artery), BA and contralateral ICA are shown. The blood from the heart enters the neck via four pathways, the right and left Common Carotid Arteries, and right and left Vertebral Arteries. Above the circle of Willis, classically, there are no collateral pathways to the six cortical regions of the brain corresponding to the six branch arteries. The branching arterial networks embrace the surface of the brain (a feature not shown in FIG. 10) before penetrating branches forming arterioles (not shown) leading to capillaries (also not shown). From the capillaries, confluences form venules and veins that converge to form the venous network returning to the cortical surface to form the venous web in the arachnoid space, ultimately connecting to the venous sinuses at the interior surface of the skull and exiting through the venous foramen on each side.

The arterial and venous systems, in some circumstances, are capable of responding to ischemia by developing new pathways. Thus, on angiography, additional arterial and venous pathways are sometimes found to and from tissues. Such additional pathways are often not included in classic anatomical descriptions, but are important patient specific features that often serve to protect from tissue ischemia. If such collateral pathways have developed in a specific patient to provide adequate perfusion to the brain and thus avoid the risk of atheroembolic stroke, the physiologic diagnostic method in this invention will not indicate that the patient is at risk for stroke even though the anatomic anomaly exists.

In this context, ischemia means insufficient blood flow to the tissues, regional hypotension means low blood pressure to the tissues compensated by a regional reduction in end-organ vascular resistance that assures sufficient blood flow. Vascular reserve (cerebrovascular reserve) means that the tissue is able to reduce resistance to flow in order to maintain blood flow when arterial hypotension is present.

Figure 14:
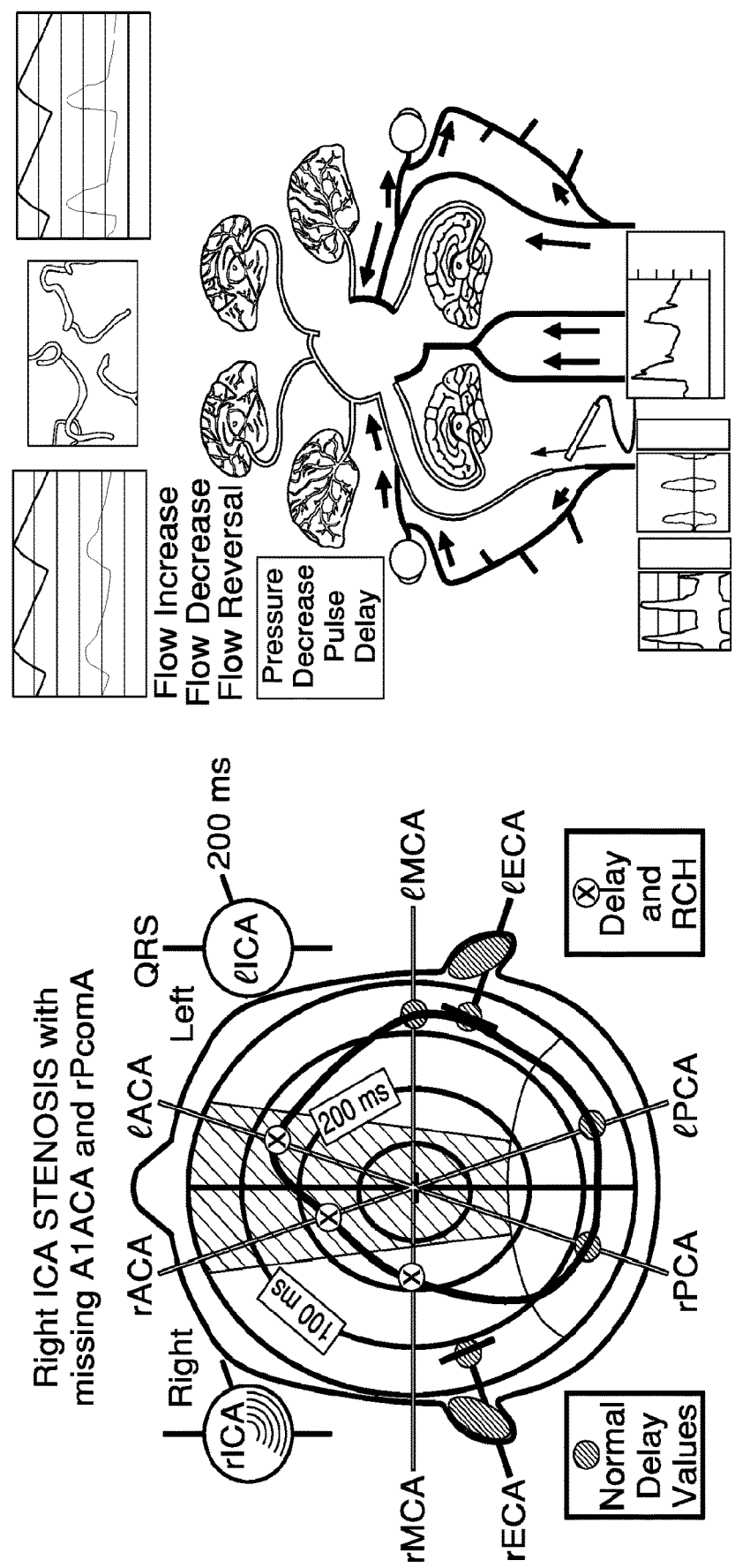
FIG. 14 shows an abnormal examination report for pressure reducing stenosis.

FIG. 14 shows an exemplary report display for a patient who suffered a primary (first) embolic stroke. The cerebral pulse delay data from this patient was obtained from an ultrasonic tissue Doppler system of a kind included in this invention. The study included an examination of over 100 people; the remainder had normal pulse delay. No data is available about the composition of the embolus, but the composition is likely to be atherosclerotic debris. No information is available about the Doppler examination of the carotid arteries or carotid bruits, the information in the diagram was taken from another patient with similar clinical presentations.

In this patient the right lateral and bilateral anterior cerebral pulsations are pathologically delayed >200 ms (indicated by "X"), but the left lateral pulsations are within normal delay limits <100 ms. From that information, it is inferred that the coW is disconnected at the right PcomA and left a1ACA as shown in the diagram at right. On the right of the figure, an angiogram is shown from such a case, and the theoretical eye pulse waveforms are displayed as well as the likely directions of blood flow. The spectral waveforms at the bottom right from the proximal ICA from a similar patient show the characteristics of systolic bruit: high amplitude low frequency bilateral systolic signal that on reduction of the Doppler pulse repetition frequency shows bidirectional harmonic Bessel function characteristics.

On the left, the icon at the right internal carotid in the neck shows a clockface icon with an indication of a high frequency (500 Hz) bruit lasting from 350 ms to 700 ms, supporting the diagnosis of a right proximal ICA pressure reducing stenosis.

Figure 15:
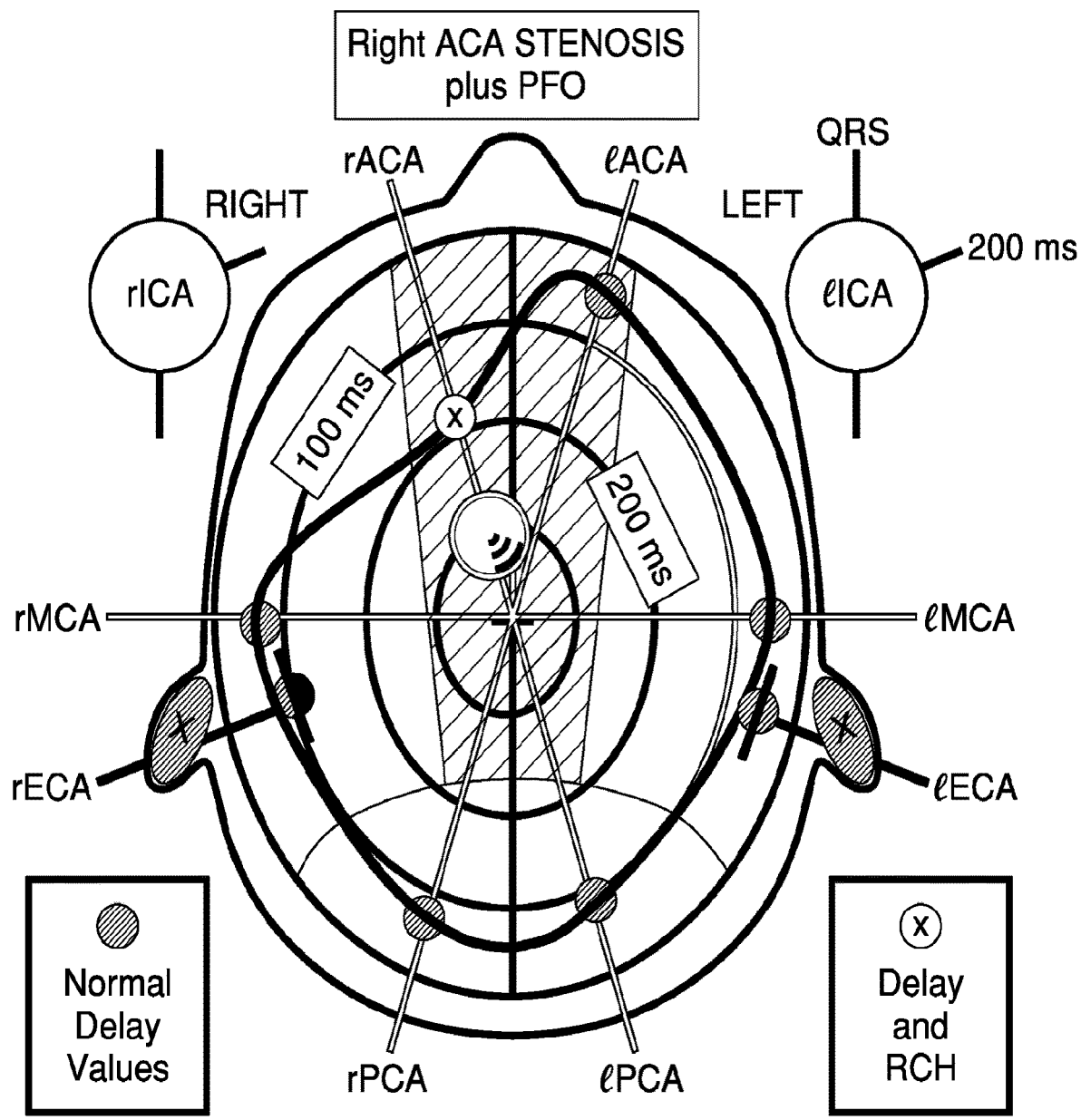
FIG. 15 shows an abnormal examination report for pulse delay.

FIG. 15 shows an exemplary report display for a hypothetical patient who is likely to suffer a primary (first) embolic stroke in the territory of the right Anterior Cerebral Artery (ACA) affecting the right frontal lobe of the brain which controls executive function (decision making) and the right medial motor and sensory cortices which connect to the left leg and foot. The bruit icon near the center of the brain indicates a low frequency bruit (150 Hz) lasting from 350 ms to 450 ms. This indicates an Anterior Cerebral Artery stenosis distal to the coW. There is currently no noninvasive method in use to identify such lesions.

In another aspect of the disclosed subject matter, we want to identify 2 types of patients: disconnected COW; and stenosis in internal Coratid artery. In these cases one portion of the brain will have delayed pulsations, and that is what we will detect. One transducer will look at each artery in the brain to look for delay (2nd thing we are looking for). If there is stenosis or obstruction of a branch artery above the COW, that could also cause a stroke. The obstruction will cause two things will happen:
1. brain tissue has pulse delay
2. vibration detectable via ultrasound or stethoscope.

We will look at deep tissue at center of brain for vibration, and shallow tissue we look for delayed pulsation. We also measure diameter of eyeball, and measure vibration and pulse delay at cerebellum (strokes here cause loss of balance). Transducers are not imaging. The transducers only tell us whether tissue is moving towards or away from sensor (Doppler transducer) and depending on how its moving we can determine whether vibration or motion exists. Measure for pressure drop can show whether shear is occurring in artery. Thus we look for vibration in COANDA. Because flow changes direction, there is a surface. We are looking for evidence of pressure drop due to pulse delay and due to turbulence which can be seen via vibration measurement. Stent placement using x-ray and dyes can then be done to treat stenosis when turbulence is seen.

Evaluation can be done automatically. Performing procedure is easy like EKG: Electrodes on chest, then EKG plotted, computer algorithm analyzes. Put headband on person with series of transducers, have to get hair out of way, and gathering data should take less than a minute.

The CortiFlow is an ultrasonic Doppler system that measures regional blood flow dynamics in real time depending on the same underlying physiology as the BOLD (Blood Oxygen Level Dopendent) MRI method for functional brain imaging. With regard to the dynamics of head trauma, the following appears to be true:
1. Measured sports head collisions of 100 G often occur, but don't cause symptoms.
2. Head collisions of 200 G are easily possible in boxing, and running, with durations of 0.5 to 5 milliseconds.
3. These conditions are similar to those that cause hydraulic cavitation producing sonoluminescence and chemical reactions. 4.

The collapse of the cavitation bubbles is marked by a 50 picosecond optical emission of "white" light and by the emission of an acoustic pulse that is detectable with a microphone. If cavitation is the primary mechanism causing the contrecoup brain concussion injury, then the event can be detected at the time of injury by a microphone to detect the sound pulse and a photodetector to detect the light sonoluminescence light impulse. It is implausible that the light could penetrate the skull, but since optical oximetry is done through the skull, the light can impulse should be able to be detected.

With regard to a method of measuring regional flow rate, the pulsatility in the arachnoid space thickness of venous blood will also affect the measurement of transcranial pulse oximetry measurements. The oxygen saturation of this venous blood varies between 45% and 75%. The arachnoid venous blood oxygenation is also the measured parameter in functional Magnetic Resonance Imaging (fMRI). The thickness of the arachnoid space is about 2.5 mm and the percent coverage of the space by veins is about 20% and the thickness pulsatility is about 0.025 mm or about 1% so the change in volume of venous blood is about 5%.

If a transcranial pulse oximeter is processed like peripheral pulse oximetry, then the measurement would be dominated by this pulsation in arachnoid venous blood, but the waveform would look like arteriolar blood. X-ray Computed Tomography images are acquired by acquiring a sequence of views of a portion of the anatomy, and projecting those views into a single image based on the assumption that during the acquisition of the sequence, no motion of the tissue occurred. But, between images, and even during the exposure time of a single image, tissue motions due to vascular pulsations, respiratory motions and muscular motions can move the tissues significant fractions of the image resolution, thus blurring the image; limiting resolution. A similar problem exists in MR imaging. By measuring the actual motions with ultrasonic tissue Doppler, or some other independent method, such as an optical method, the effect of the motions can be computed and the effect can be compensated or cancelled.

One method of compensation is to trigger the image exposures to occur at the same tissue position. This can be done when tissue motion is periodic, such as pulsatile, so that the successive exposures are "gated" to the same time in the cycle. Currently, gating is done by using the ECG-QRS as the time reference. Although this provides an indirect timing reference, using the displacement of the imaged tissue is more direct and thus superior.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. An adhesive contact pad comprising:
an envelope that includes a transducer envelope surface and a skin envelope surface, the transducer envelope surface being on an opposing side of the envelope relative to the skin envelope surface;
a first adhesive, associated with the transducer envelope surface, provided to attach a transducer to the adhesive contact pad;
a second adhesive, associated with the skin envelope surface, provided to attach the adhesive contact pad to the skin of a patient;
viscous fluid that is disposed in an interior of the envelope; and
the envelop further including a removable portion, and the removable portion configured such that a user may remove the removable portion so as to allow air into the envelope,
such entry of air into the envelope allowing independent deformation of the skin envelope surface from the transducer envelope surface.

2. The adhesive contact pad of claim 1, wherein the removable portion includes a zip-tear.

3. The adhesive contact pad of claim 2, wherein the zip-tear is positioned on an exposed edge of the envelope.

4. The adhesive contact pad of claim 1, wherein the envelope is in the form of a flat envelope.

5. The adhesive contact pad of claim 1, wherein the viscous fluid is a thin layer of viscous gel, and gas is excluded from the interior of the envelop prior to the removable portion being removed.

6. The adhesive contact pad of claim 1, wherein the viscous fluid is a thin layer of viscous gel.

7. The adhesive contact pad of claim 1, wherein the first adhesive is a biologically compatible adhesive.

* * * * *